(12) United States Patent  
McGuckin, Jr. et al.

(10) Patent No.: US 7,037,316 B2
(45) Date of Patent: May 2, 2006

(54) ROTATIONAL THROMBECTOMY DEVICE

(76) Inventors: James F. McGuckin, Jr., 585 County Line Rd., Radnor, PA (US) 19087; Peter W. H. Hinchliffe, 927 Brittney Ter., Downington, PA (US) 19335; Walter H. Peters, 1206 New Hampshire La., Downington, PA (US) 19335

( * ) Notice: Subject to any disclaimer, the term of this patent is extended or adjusted under 35 U.S.C. 154(b) by 490 days.

(21) Appl. No.: 10/113,248

(22) Filed: Apr. 1, 2002

(65) Prior Publication Data

US 2002/0173812 A1 Nov. 21, 2002

Related U.S. Application Data

(63) Continuation-in-part of application No. 09/888,149, filed on Jun. 22, 2001, which is a continuation-in-part of application No. PCT/US00/41355, filed on Oct. 20, 2000, which is a continuation-in-part of application No. 09/502,261, filed on Feb. 11, 2000, now Pat. No. 6,602,264, which is a continuation of application No. 09/122,483, filed on Jul. 23, 1998, now Pat. No. 6,090,118.

(60) Provisional application No. 60/214,331, filed on Jun. 27, 2000, provisional application No. 60/161,124, filed on Oct. 22, 1999, and provisional application No. 60/053,475, filed on Jul. 24, 1997.

(51) Int. Cl.
*A61B 17/22* (2006.01)

(52) U.S. Cl. ....................... 606/159; 606/113
(58) Field of Classification Search ................ 606/159, 606/170, 174, 180, 113, 114, 127
See application file for complete search history.

(56) References Cited

U.S. PATENT DOCUMENTS 2,756,752 A 7/1956 Scherlis (Continued)

FOREIGN PATENT DOCUMENTS

DE 3640034 5/1988

(Continued)

OTHER PUBLICATIONS

Rex Medical website—www.rexmedical.com—home page (Jul. 2000).
Bacchus Vascular Solera Thrombectomy Catheter Brochure (Jan. 4, 2002).

*Primary Examiner*—Kevin T. Truong
(74) *Attorney, Agent, or Firm*—Lerner, David, Littenberg, Krumholz & Mentlik, LLP

(57) ABSTRACT

A thrombectomy apparatus for breaking up thrombus or other obstructive material in a lumen of a vascular graft or vessel comprising a flexible sheath, and a wire positioned within the flexible sheath wherein the wire and flexible sheath are relatively movable. The wire is substantially sinuous in configuration and assumes a substantially sinuous shape when in the deployed position and assumes a straighter position in the retracted position. The wire is operatively connected to a motor for rotation of the wire to enable peaks of the sinuous wire to contact a wall of the lumen to break up the thrombus or other obstructive material.

23 Claims, 12 Drawing Sheets

U.S. PATENT DOCUMENTS

| | | |
|---|---|---|
| 3,108,594 A | 10/1963 | Glassman |
| 3,612,058 A | 10/1971 | Ackerman |
| 3,741,214 A | 6/1973 | Tillander |
| 3,749,085 A | 7/1973 | Willson et al. |
| 3,841,308 A | 10/1974 | Tate |
| 4,030,503 A | 6/1977 | Clark, III |
| 4,559,046 A | 12/1985 | Groshong et al. |
| 4,579,127 A | 4/1986 | Haacke |
| 4,614,188 A | 9/1986 | Bazell et al. |
| 4,646,736 A | 3/1987 | Auth |
| 4,664,112 A | 5/1987 | Kensey et al. |
| 4,676,778 A | 6/1987 | Nelson, Jr. |
| 4,706,671 A | 11/1987 | Weinrib |
| 4,732,154 A | 3/1988 | Shiber |
| 4,745,919 A | 5/1988 | Bundy et al. |
| 4,794,928 A | 1/1989 | Kletschka |
| 4,819,634 A | 4/1989 | Shiber |
| 4,883,460 A | 11/1989 | Zanetti |
| 4,935,025 A | 6/1990 | Bundy et al. |
| 4,984,581 A | 1/1991 | Stice |
| 4,986,807 A | 1/1991 | Farr |
| 4,994,067 A | 2/1991 | Summers |
| 5,002,553 A | 3/1991 | Shiber |
| RE33,569 E | 4/1991 | Gifford et al. |
| 5,007,896 A | 4/1991 | Shiber |
| 5,009,659 A | 4/1991 | Hamlin et al. |
| 5,011,488 A | 4/1991 | Ginsburg |
| 5,011,489 A | 4/1991 | Salem |
| 5,011,490 A | 4/1991 | Fischell et al. |
| 5,019,088 A | 5/1991 | Farr |
| 5,019,089 A | 5/1991 | Farr |
| 5,024,651 A | 6/1991 | Shiber |
| 5,026,383 A | 6/1991 | Nobles |
| 5,026,384 A | 6/1991 | Farr et al. |
| 5,041,217 A | 8/1991 | Reid |
| 5,042,984 A | 8/1991 | Kensey et al. |
| 5,047,040 A | 9/1991 | Simpson et al. |
| 5,047,041 A | 9/1991 | Samuels |
| 5,049,124 A | 9/1991 | Bales |
| 5,049,154 A | 9/1991 | Quadri |
| 5,053,044 A | 10/1991 | Mueller et al. |
| 5,054,501 A | 10/1991 | Chuttani et al. |
| 5,059,203 A | 10/1991 | Husted |
| 5,061,240 A | 10/1991 | Cherian |
| 5,062,648 A | 11/1991 | Gomringer |
| 5,069,662 A | 12/1991 | Bodden |
| 5,069,679 A | 12/1991 | Taheri |
| 5,071,424 A | 12/1991 | Reger |
| 5,071,425 A | 12/1991 | Gifford et al. |
| 5,074,841 A | 12/1991 | Ademovic et al. |
| 5,078,722 A | 1/1992 | Stevens |
| 5,078,723 A | 1/1992 | Dance et al. |
| 5,084,010 A | 1/1992 | Plaia et al. |
| 5,085,662 A | 2/1992 | Willard |
| 5,087,264 A | 2/1992 | Miller et al. |
| 5,087,265 A | 2/1992 | Summers |
| 5,092,839 A | 3/1992 | Kipperman |
| 5,092,872 A | 3/1992 | Segalowitz |
| 5,092,873 A | 3/1992 | Simpson et al. |
| 5,097,849 A | 3/1992 | Kensey et al. |
| 5,100,423 A | 3/1992 | Fearnot |
| 5,100,424 A | 3/1992 | Jang et al. |
| 5,100,425 A | 3/1992 | Fischell et al. |
| 5,100,426 A | 3/1992 | Nixon |
| 5,102,415 A | 4/1992 | Guenther et al. |
| 5,108,411 A | 4/1992 | McKenzie |
| 5,108,419 A | 4/1992 | Reger et al. |
| 5,112,347 A | 5/1992 | Taheri |
| 5,114,399 A | 5/1992 | Kovalcheck |
| 5,116,350 A | 5/1992 | Stevens |
| 5,116,352 A | 5/1992 | Schnepp-Pesch et al. |
| 5,127,902 A | 7/1992 | Fischell |
| 5,127,917 A | 7/1992 | Niederhauser et al. |
| 5,131,379 A | 7/1992 | Sewell |
| 5,133,725 A | 7/1992 | Quadri |
| 5,135,482 A | 8/1992 | Neracher |
| 5,135,484 A | 8/1992 | Wright |
| 5,135,531 A | 8/1992 | Shiber |
| 5,139,506 A | 8/1992 | Bush |
| 5,141,491 A | 8/1992 | Bowald |
| 5,141,503 A | 8/1992 | Sewell |
| 5,152,771 A | 10/1992 | Sabbaghian et al. |
| 5,152,772 A | 10/1992 | Sewell |
| 5,152,773 A | 10/1992 | Redha |
| 5,154,724 A | 10/1992 | Andrews |
| 5,156,610 A | 10/1992 | Reger |
| 5,158,564 A | 10/1992 | Schnepp-Pesch et al. |
| 5,160,342 A | 11/1992 | Reger et al. |
| 5,163,421 A | 11/1992 | Bernstein et al. |
| 5,170,805 A | 12/1992 | Kensey et al. |
| 5,171,316 A | 12/1992 | Mehigan |
| 5,176,693 A | 1/1993 | Pannek, Jr. |
| 5,178,625 A | 1/1993 | Groshong |
| 5,181,920 A | 1/1993 | Mueller et al. |
| 5,192,268 A | 3/1993 | Shiber |
| 5,192,290 A | 3/1993 | Hilal |
| 5,192,291 A | 3/1993 | Pannek |
| 5,195,954 A | 3/1993 | Schnepp-Pesch et al. |
| 5,195,956 A | 3/1993 | Stockmeier |
| 5,196,024 A | 3/1993 | Barath |
| 5,197,485 A | 3/1993 | Grooters |
| 5,201,750 A | 4/1993 | Hecherl et al. |
| 5,209,749 A | 5/1993 | Buelna |
| 5,211,651 A | 5/1993 | Reger et al. |
| 5,211,683 A | 5/1993 | Maginot |
| 5,217,026 A | 6/1993 | Stoy et al. |
| 5,217,453 A | 6/1993 | Wilk |
| 5,217,474 A | 6/1993 | Zacca et al. |
| 5,222,965 A | 6/1993 | Haughton |
| 5,222,966 A | 6/1993 | Perkins et al. |
| 5,224,945 A | 7/1993 | Pannek |
| 5,224,949 A | 7/1993 | Gomringer et al. |
| 5,226,909 A | 7/1993 | Evans et al. |
| 5,234,450 A | 8/1993 | Segalowitz |
| 5,234,451 A | 8/1993 | Osypka |
| 5,242,460 A | 9/1993 | Klein et al. |
| 5,242,461 A | 9/1993 | Kortenbach et al. |
| 5,248,296 A | 9/1993 | Alliger |
| 5,250,059 A | 10/1993 | Andreas et al. |
| 5,250,060 A | 10/1993 | Carbo et al. |
| 5,251,640 A | 10/1993 | Osborne |
| 5,261,877 A | 11/1993 | Fine et al. |
| 5,262,593 A | 11/1993 | Madry et al. |
| 5,267,954 A | 12/1993 | Nita |
| 5,269,751 A | 12/1993 | Kaliman et al. |
| 5,269,793 A | 12/1993 | Simpson |
| 5,282,484 A | 2/1994 | Reger |
| 5,282,813 A | 2/1994 | Redha |
| 5,284,478 A | 2/1994 | Nobles et al. |
| 5,284,486 A | 2/1994 | Kotula et al. |
| 5,295,958 A | 3/1994 | Shturman |
| 5,300,025 A | 4/1994 | Wantink |
| 5,303,719 A | 4/1994 | Wilk et al. |
| 5,304,189 A | 4/1994 | Goldberg et al. |
| 5,304,220 A | 4/1994 | Maginot |
| 5,306,244 A | 4/1994 | Shiber |
| 5,308,354 A | 5/1994 | Zacca et al. |
| 5,312,425 A | 5/1994 | Evans et al. |
| 5,312,427 A | 5/1994 | Shturman |
| 5,313,967 A | 5/1994 | Lieber et al. |
| 5,314,407 A | 5/1994 | Auth et al. |

| | | | | | |
|---|---|---|---|---|---|
| 5,314,438 A | 5/1994 | Shturman | 5,527,327 A | 6/1996 | Louw et al. |
| 5,318,576 A | 6/1994 | Plassche et al. | 5,527,330 A | 6/1996 | Tovey |
| 5,320,599 A | 6/1994 | Griep et al. | 5,536,242 A | 7/1996 | Willard et al. |
| 5,320,634 A | 6/1994 | Vigil et al. | 5,540,656 A | 7/1996 | Pflueger et al. |
| 5,334,211 A | 8/1994 | Shiber | 5,540,707 A | 7/1996 | Ressemann et al. |
| 5,336,167 A | 8/1994 | Sullivan et al. | 5,542,917 A | 8/1996 | Nita et al. |
| 5,336,234 A | 8/1994 | Vigil et al. | 5,542,925 A | 8/1996 | Orth |
| 5,342,394 A | 8/1994 | Matsuno et al. | 5,547,469 A | 8/1996 | Rowland et al. |
| 5,344,395 A | 9/1994 | Whalen et al. | 5,551,443 A | 9/1996 | Sepetka et al. |
| 5,345,940 A | 9/1994 | Seward et al. | 5,554,163 A | 9/1996 | Shturman |
| 5,345,945 A | 9/1994 | Hodgson et al. | 5,556,405 A | 9/1996 | Lary |
| 5,346,473 A | 9/1994 | Bowman | 5,556,408 A | 9/1996 | Farhat |
| 5,348,017 A | 9/1994 | Thornton et al. | 5,562,275 A | 10/1996 | Weissenfluh et al. |
| 5,350,390 A | 9/1994 | Sher | 5,562,701 A | 10/1996 | Huiteme et al. |
| 5,352,232 A | 10/1994 | Cohen | 5,569,204 A | 10/1996 | Cramer |
| 5,356,418 A | 10/1994 | Shturman | 5,569,275 A | 10/1996 | Kotula et al. |
| 5,358,472 A | 10/1994 | Vance et al. | 5,569,276 A | 10/1996 | Jang et al. |
| 5,358,485 A | 10/1994 | Vance et al. | 5,569,277 A | 10/1996 | Evans et al. |
| 5,358,507 A | 10/1994 | Daily | 5,569,279 A | 10/1996 | Rainin |
| 5,358,509 A | 10/1994 | Fine et al. | 5,571,122 A | 11/1996 | Kelly et al. |
| 5,360,432 A | 11/1994 | Shturman | 5,571,130 A | 11/1996 | Simpson et al. |
| 5,360,433 A | 11/1994 | Medl | 5,571,167 A | 11/1996 | Maginot |
| 5,366,463 A | 11/1994 | Ryan | 5,584,842 A | 12/1996 | Fogarty et al. |
| 5,366,464 A | 11/1994 | Belknap | 5,584,843 A | 12/1996 | Wulfman et al. |
| 5,368,603 A | 11/1994 | Halliburton | 5,591,183 A | 1/1997 | Chin |
| 5,370,609 A | 12/1994 | Drasler et al. | 5,591,184 A | 1/1997 | McDonnell et al. |
| 5,370,651 A | 12/1994 | Summers | 5,599,307 A | 2/1997 | Bacher et al. |
| 5,370,653 A | 12/1994 | Cragg | 5,601,580 A | 2/1997 | Goldberg et al. |
| 5,372,144 A | 12/1994 | Mortier et al. | 5,601,581 A | 2/1997 | Fogarty et al. |
| 5,372,601 A | 12/1994 | Lary | 5,605,162 A | 2/1997 | Mirzaee et al. |
| 5,383,460 A | 1/1995 | Jang et al. | 5,609,602 A | 3/1997 | Machemer et al. |
| 5,395,311 A * | 3/1995 | Andrews .................... 606/159 | 5,616,149 A | 4/1997 | Barath |
| 5,395,315 A | 3/1995 | Griep | 5,622,188 A | 4/1997 | Plaia et al. |
| 5,395,384 A | 3/1995 | Duthoit | 5,624,455 A | 4/1997 | Matsuno |
| 5,402,790 A | 4/1995 | Jang et al. | 5,624,457 A | 4/1997 | Farley et al. |
| 5,403,334 A | 4/1995 | Evans et al. | 5,626,562 A | 5/1997 | Castro |
| 5,409,454 A | 4/1995 | Fischell et al. | 5,626,593 A | 5/1997 | Imran |
| 5,411,509 A | 5/1995 | Hilal | 5,626,597 A | 5/1997 | Urban et al. |
| 5,417,703 A | 5/1995 | Brown et al. | 5,628,746 A | 5/1997 | Clayman |
| 5,419,774 A | 5/1995 | Willard et al. | 5,628,761 A | 5/1997 | Rizik |
| 5,423,799 A | 6/1995 | Shiu | 5,630,823 A | 5/1997 | Schmitz-Rode et al. |
| 5,423,838 A | 6/1995 | Willard | 5,632,755 A | 5/1997 | Nordgren et al. |
| 5,429,136 A | 7/1995 | Milo et al. | 5,643,199 A | 7/1997 | Rowland et al. |
| 5,441,510 A | 8/1995 | Simpson et al. | 5,643,296 A | 7/1997 | Hundertmark et al. |
| 5,449,369 A | 9/1995 | Imran | 5,643,297 A | 7/1997 | Nordgren et al. |
| 5,449,372 A | 9/1995 | Schmaltz et al. | 5,643,298 A | 7/1997 | Nordgren et al. |
| 5,451,208 A | 9/1995 | Goldrath | 5,649,941 A | 7/1997 | Lary |
| 5,453,088 A | 9/1995 | Boudewijn et al. | 5,649,946 A | 7/1997 | Bramlet |
| 5,462,529 A | 10/1995 | Simpson et al. | 5,653,722 A | 8/1997 | Kieturakis |
| 5,476,450 A | 12/1995 | Ruggio | 5,658,282 A | 8/1997 | Daw et al. |
| 5,480,370 A | 1/1996 | Gelsinger | 5,658,301 A | 8/1997 | Lemaitre et al. |
| 5,484,412 A | 1/1996 | Pierpont | 5,658,302 A | 8/1997 | Wicherski et al. |
| 5,488,958 A | 2/1996 | Topel et al. | 5,662,603 A | 9/1997 | Gelbfish |
| 5,490,859 A | 2/1996 | Mische et al. | 5,662,671 A | 9/1997 | Barbut et al. |
| 5,496,267 A | 3/1996 | Drasler et al. | 5,662,701 A | 9/1997 | Plaia et al. |
| 5,497,782 A | 3/1996 | Fugoso | 5,665,093 A | 9/1997 | Atkins |
| 5,501,694 A | 3/1996 | Ressemann et al. | 5,665,098 A | 9/1997 | Kelly et al. |
| 5,507,292 A | 4/1996 | Jang et al. | 5,667,480 A | 9/1997 | Knight et al. |
| 5,507,760 A | 4/1996 | Wynne et al. | 5,669,920 A | 9/1997 | Conley |
| 5,507,761 A | 4/1996 | Duer | 5,674,226 A | 10/1997 | Doherty et al. |
| 5,512,044 A | 4/1996 | Duer | 5,674,232 A | 10/1997 | Halliburton |
| 5,514,092 A | 5/1996 | Forman et al. | 5,681,335 A | 10/1997 | Serra et al. |
| 5,514,115 A | 5/1996 | Frantzen et al. | 5,681,336 A | 10/1997 | Clement et al. |
| 5,514,150 A | 5/1996 | Rostoker | 5,683,362 A | 11/1997 | Rowland et al. |
| 5,514,151 A | 5/1996 | Fogarty et al. | 5,688,234 A | 11/1997 | Frisbie |
| 5,520,635 A | 5/1996 | Gelbfish | 5,695,506 A | 12/1997 | Pike et al. |
| 5,522,824 A | 6/1996 | Ashby | 5,695,507 A | 12/1997 | Auth et al. |
| 5,522,825 A | 6/1996 | Kropf et al. | 5,695,508 A | 12/1997 | Chigogidze |
| 5,522,826 A | 6/1996 | Daily | 5,695,514 A | 12/1997 | Chin |
| 5,527,325 A | 6/1996 | Conley et al. | 5,697,944 A | 12/1997 | Lary |
| 5,527,326 A | 6/1996 | Hermann et al. | 5,700,240 A | 12/1997 | Barwick et al. |

| | | | | | | |
|---|---|---|---|---|---|---|
| 5,702,412 A | 12/1997 | Popov et al. | | 6,113,614 A | 9/2000 | Mears |
| 5,702,413 A | 12/1997 | Lafontaine | | 6,126,635 A | 10/2000 | Simpson et al. |
| 5,728,123 A | 3/1998 | Lemelson et al. | | 6,129,750 A | 10/2000 | Tockman et al. |
| 5,733,296 A | 3/1998 | Rogers et al. | | 6,143,009 A | 11/2000 | Shiber |
| 5,746,758 A | 5/1998 | Nordgren et al. | | 6,146,396 A | 11/2000 | Konya et al. |
| 5,755,968 A | 5/1998 | Stone | | 6,146,397 A | 11/2000 | Harkrider, Jr. |
| 5,766,191 A | 6/1998 | Trerotola | | 6,152,909 A | 11/2000 | Bagaoisan et al. |
| 5,766,192 A | 6/1998 | Zacca | | 6,156,046 A * | 12/2000 | Passafaro et al. ........... 606/159 |
| 5,776,153 A | 7/1998 | Rees | | 6,168,570 B1 | 1/2001 | Ferrera |
| 5,830,156 A | 11/1998 | Ali | | 6,183,487 B1 | 2/2001 | Barry et al. |
| 5,833,631 A | 11/1998 | Nguyen | | 6,185,449 B1 | 2/2001 | Berg et al. |
| 5,833,644 A | 11/1998 | Zadno-Azizi et al. | | 6,193,735 B1 | 2/2001 | Stevens |
| 5,840,046 A | 11/1998 | Deem | | 6,203,561 B1 | 3/2001 | Ramee et al. |
| 5,843,103 A | 12/1998 | Wulfman | | 6,206,898 B1 | 3/2001 | Honeycutt et al. |
| 5,876,413 A | 3/1999 | Fogarty et al. | | 6,217,595 B1 | 4/2001 | Shturman et al. |
| 5,876,414 A | 3/1999 | Straub | | 6,231,588 B1 | 5/2001 | Zadno-Azizi |
| 5,882,329 A | 3/1999 | Patterson et al. | | 6,238,405 B1 | 5/2001 | Findlay, III et al. |
| 5,885,227 A | 3/1999 | Finlayson | | 6,251,086 B1 | 6/2001 | Cornelius et al. |
| 5,895,398 A | 4/1999 | Wensel et al. | | 6,254,550 B1 | 7/2001 | McNamara et al. |
| 5,902,263 A | 5/1999 | Patterson et al. | | 6,264,667 B1 | 7/2001 | McGuckin, Jr. |
| 5,904,679 A | 5/1999 | Clayman | | 6,270,509 B1 | 8/2001 | Barry et al. |
| 5,910,364 A | 6/1999 | Miyata et al. | | 6,287,271 B1 | 9/2001 | Dubrul et al. |
| 5,916,166 A | 6/1999 | Reiss et al. | | 6,299,623 B1 | 10/2001 | Wulfman |
| 5,919,163 A | 7/1999 | Glickman | | 6,322,572 B1 | 11/2001 | Lee |
| 5,938,623 A | 8/1999 | Quiachon et al. | | 6,371,928 B1 | 4/2002 | Mcfann et al. |
| 5,941,869 A | 8/1999 | Patterson et al. | | 6,402,745 B1 | 6/2002 | Wilk |
| 5,947,985 A | 9/1999 | Imran | | 6,454,775 B1 | 9/2002 | Demarais et al. |
| 5,954,737 A | 9/1999 | Lee | | 6,454,779 B1 | 9/2002 | Taylor |
| 5,971,991 A | 10/1999 | Sunderland | | 6,482,215 B1 | 11/2002 | Shiber |
| 5,972,019 A | 10/1999 | Engelson et al. | | 6,485,500 B1 | 11/2002 | Kokish et al. |
| 5,984,877 A | 11/1999 | Fleischhacker, Jr. | | 6,663,613 B1 | 12/2003 | Evans et al. |
| 6,001,068 A | 12/1999 | Uchino et al. | | 2001/0031981 A1 | 10/2001 | DeMarais et al. |
| 6,001,112 A | 12/1999 | Taylor | | 2002/0165567 A1 | 11/2002 | Shiber |
| 6,004,279 A | 12/1999 | Crowley et al. | | | | |
| 6,019,736 A | 2/2000 | Avellanet et al. | | | | |
| 6,022,336 A | 2/2000 | Zadno-Azizi et al. | | | | |
| 6,022,363 A | 2/2000 | Walker et al. | | | | |
| 6,030,397 A | 2/2000 | Monetti et al. | | | | |
| 6,036,708 A | 3/2000 | Sciver | | | | |
| 6,056,721 A | 5/2000 | Shulze | | | | |
| 6,066,158 A | 5/2000 | Engelson et al. | | | | |
| 6,080,170 A | 6/2000 | Nash et al. | | | | |
| RE36,764 E | 7/2000 | Zacca et al. | | | | |
| 6,102,884 A | 8/2000 | Squitieri | | | | |

FOREIGN PATENT DOCUMENTS

| | | |
|---|---|---|
| DE | 8900494 | 4/1989 |
| EP | 0 177 782 A | 4/1986 |
| EP | 0452631 | 2/1991 |
| EP | 0709110 | 5/1996 |
| EP | 0815894 | 1/1998 |
| WO | WO9923958 | 5/1999 |
| WO | WO-01/54754 A | 8/2001 |

* cited by examiner

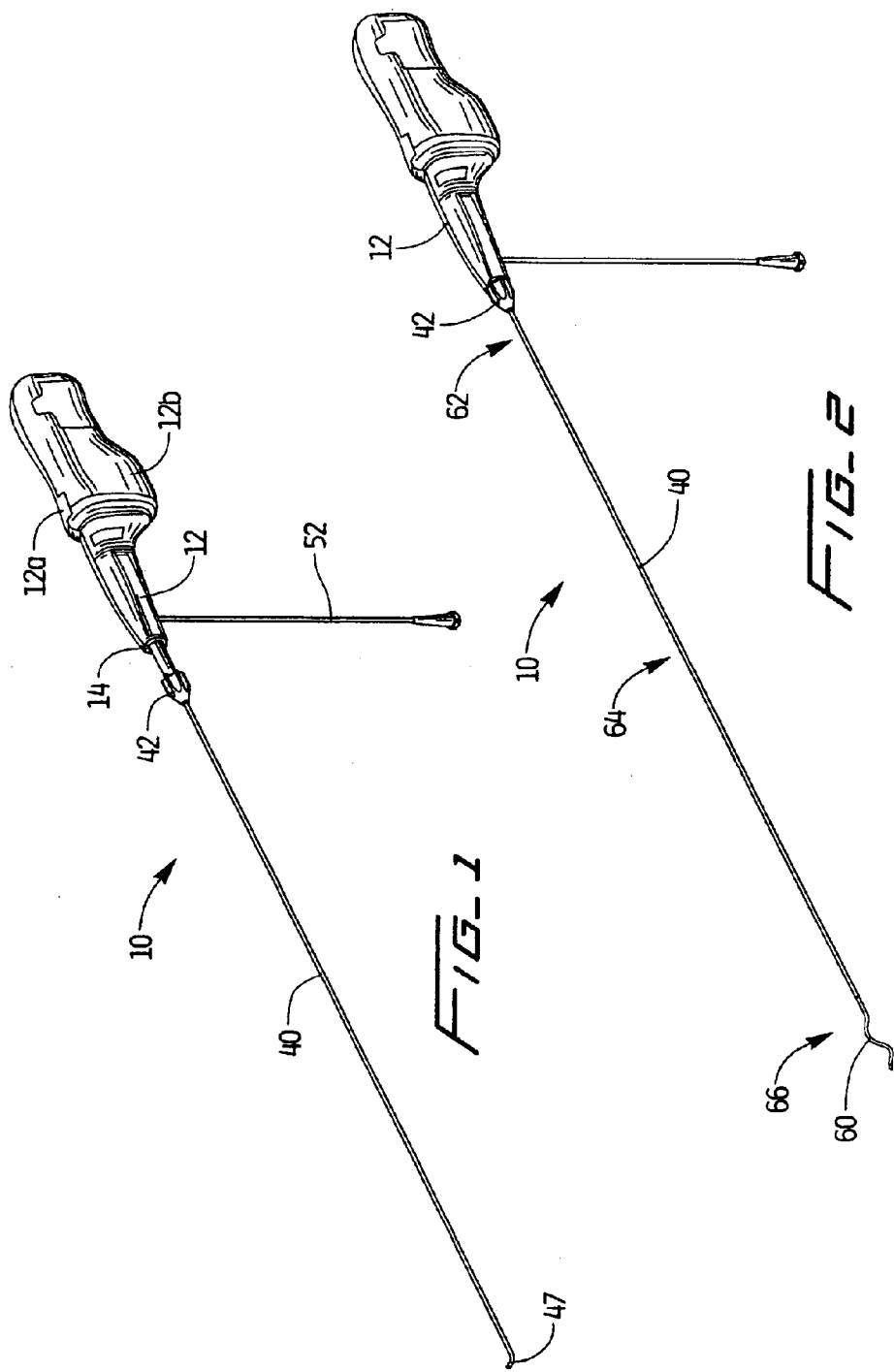

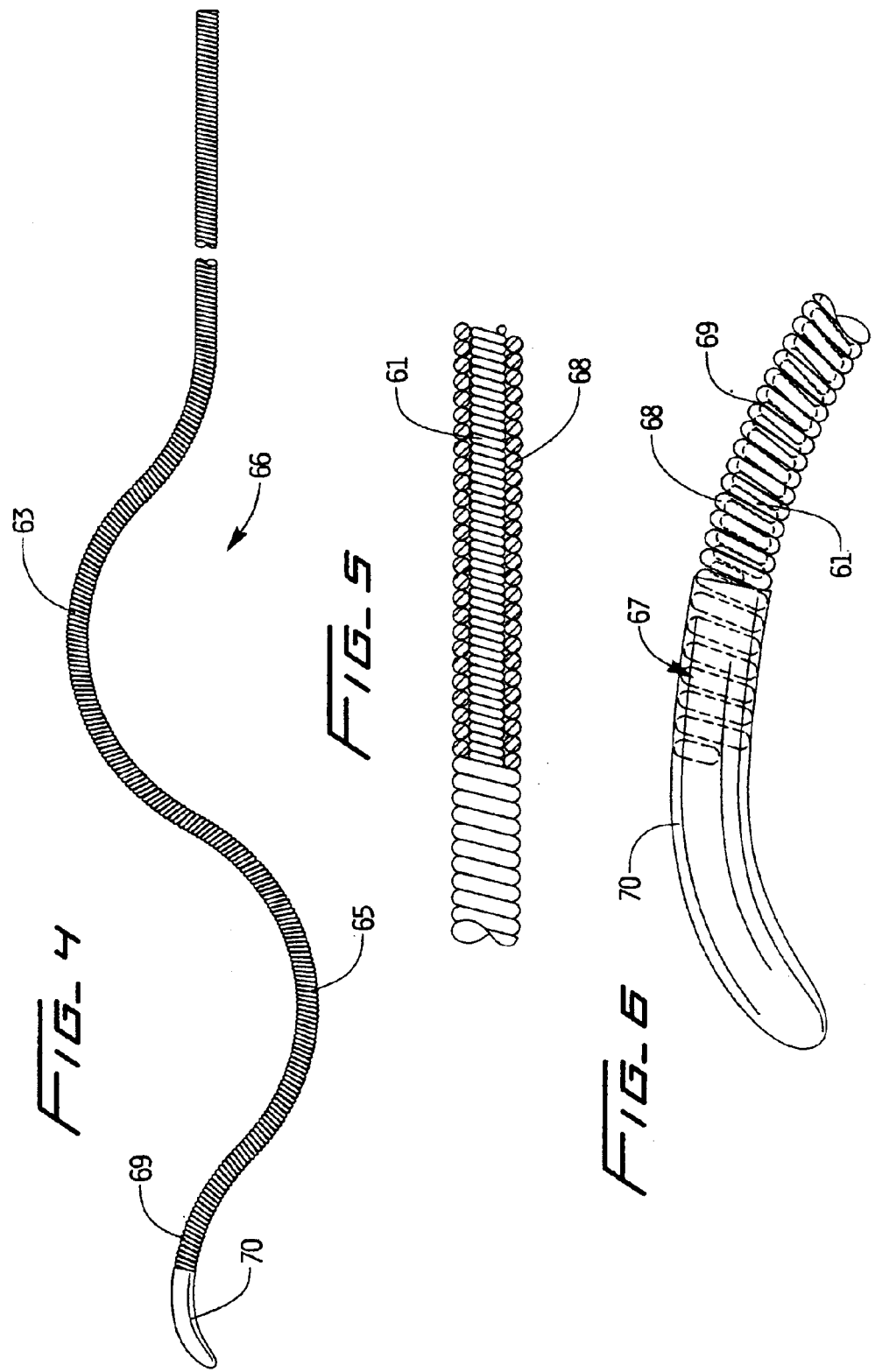

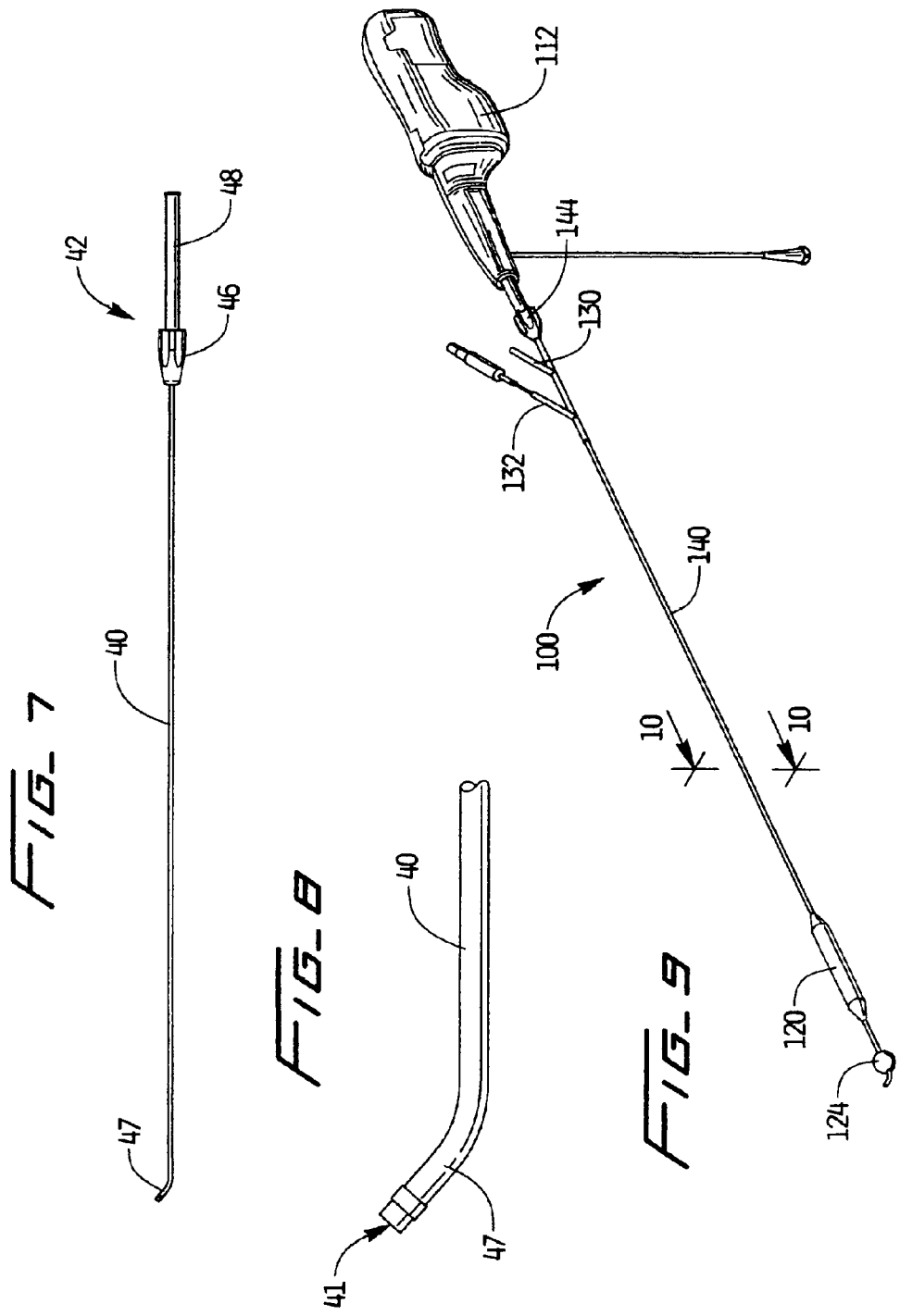

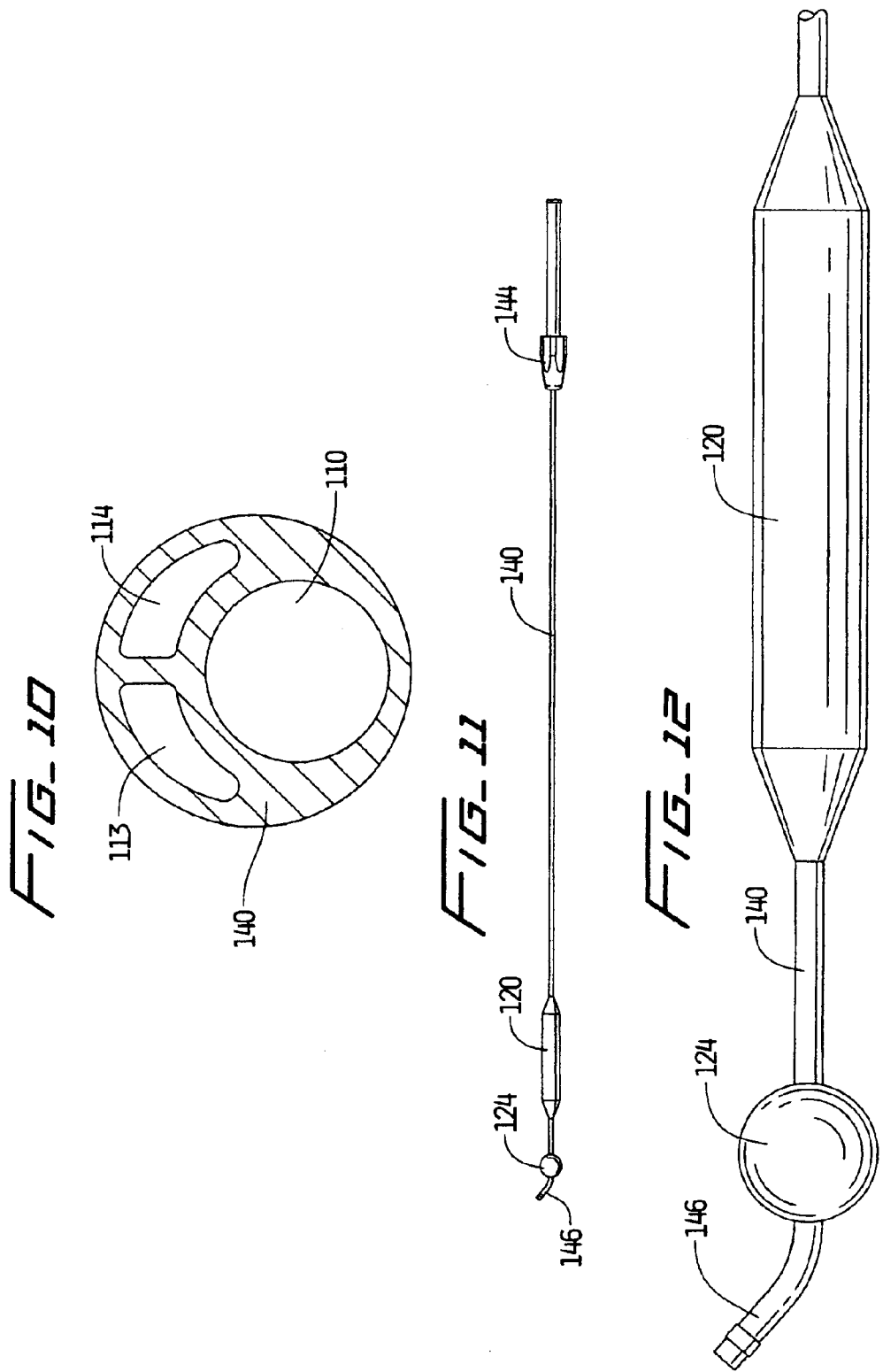

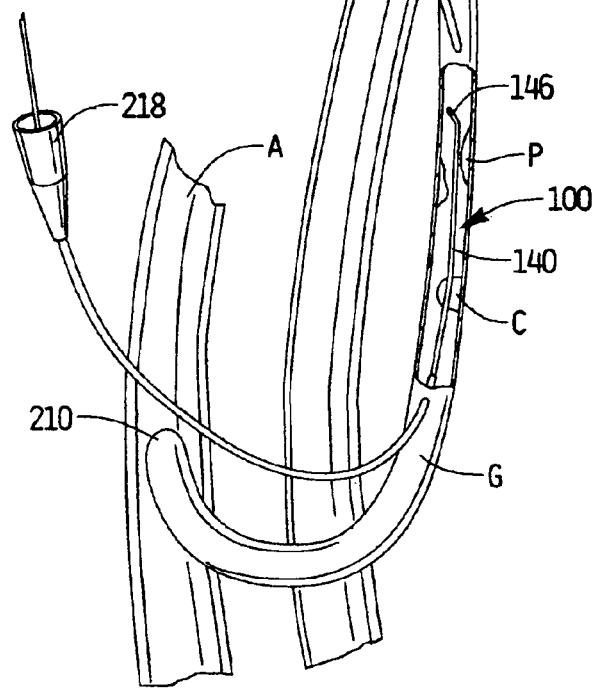
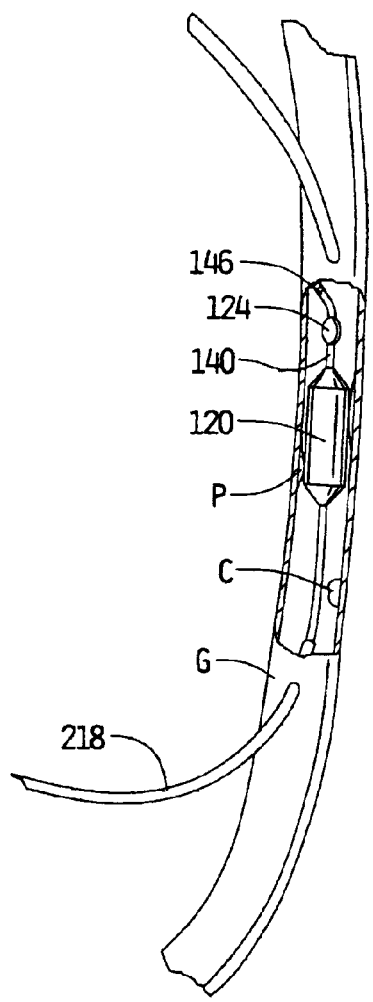

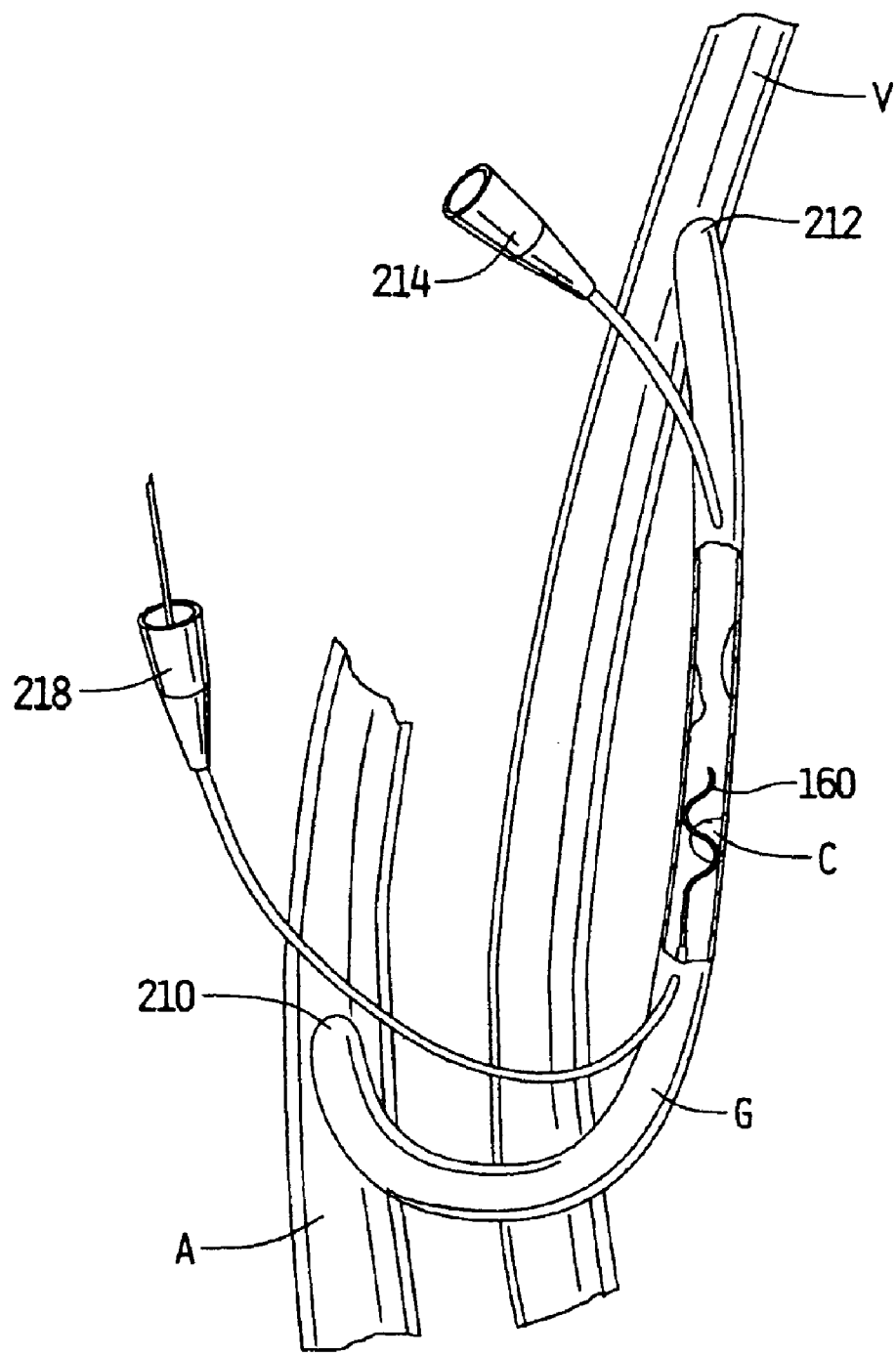
FIG_15

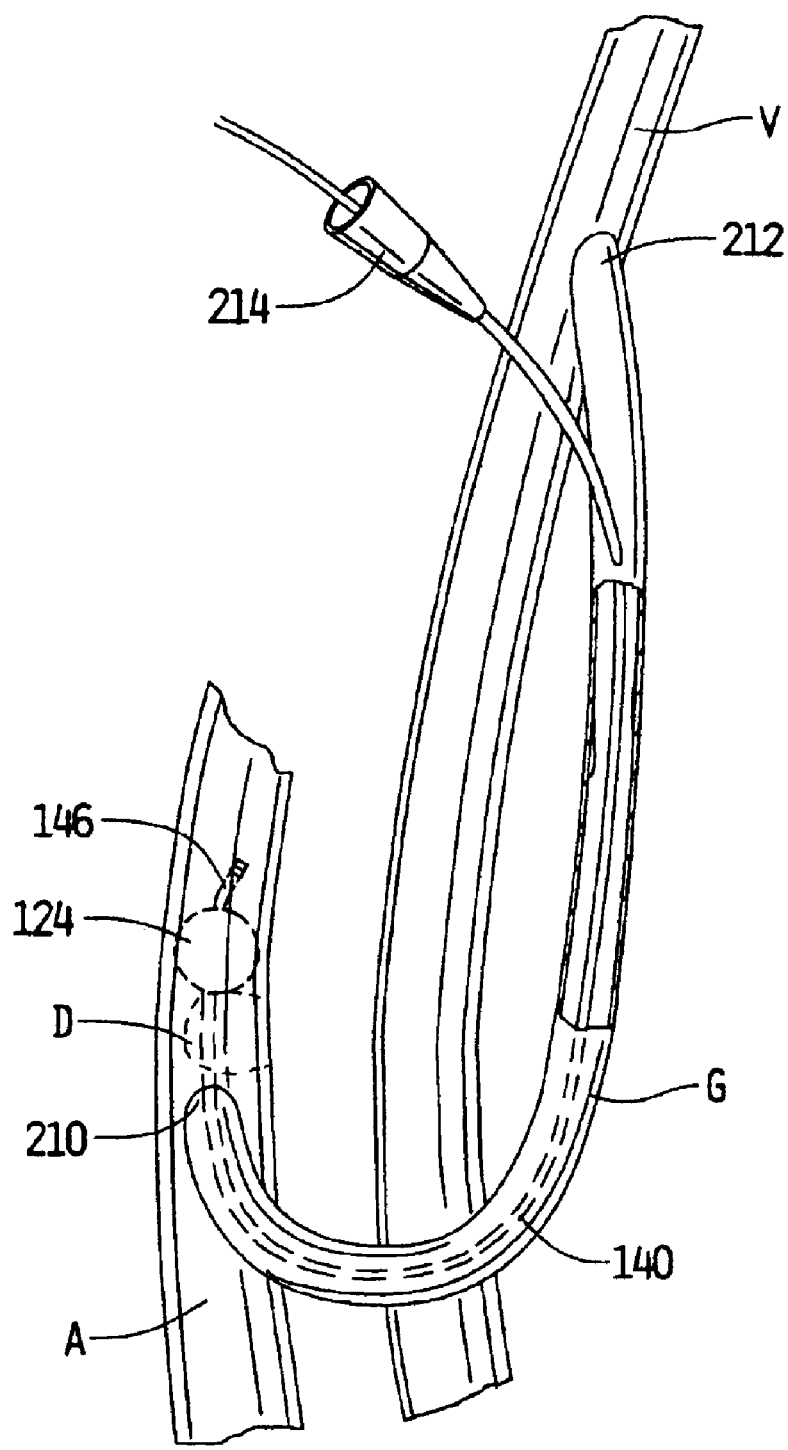
FIG_16

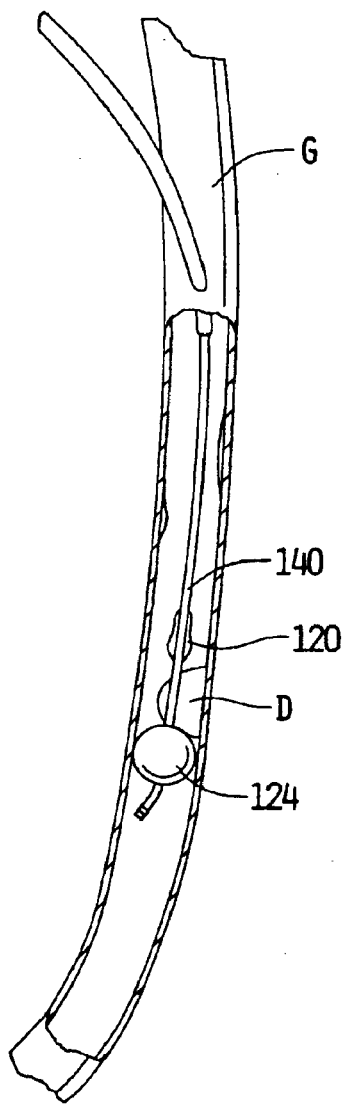
FIG_17
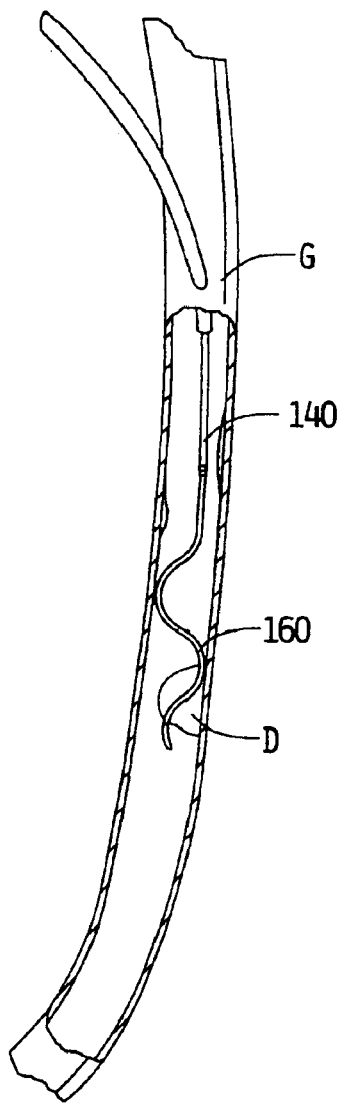
FIG_18

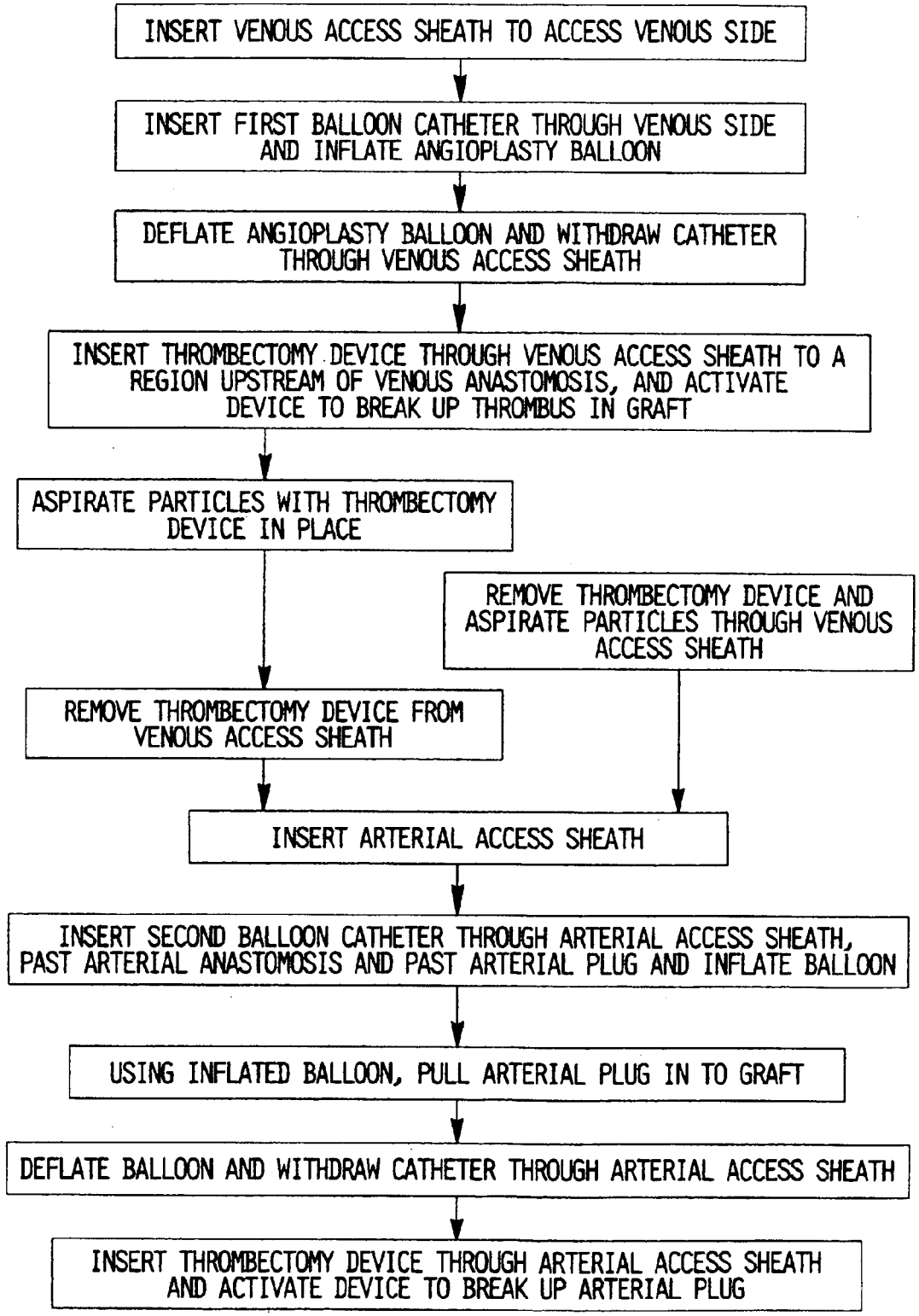

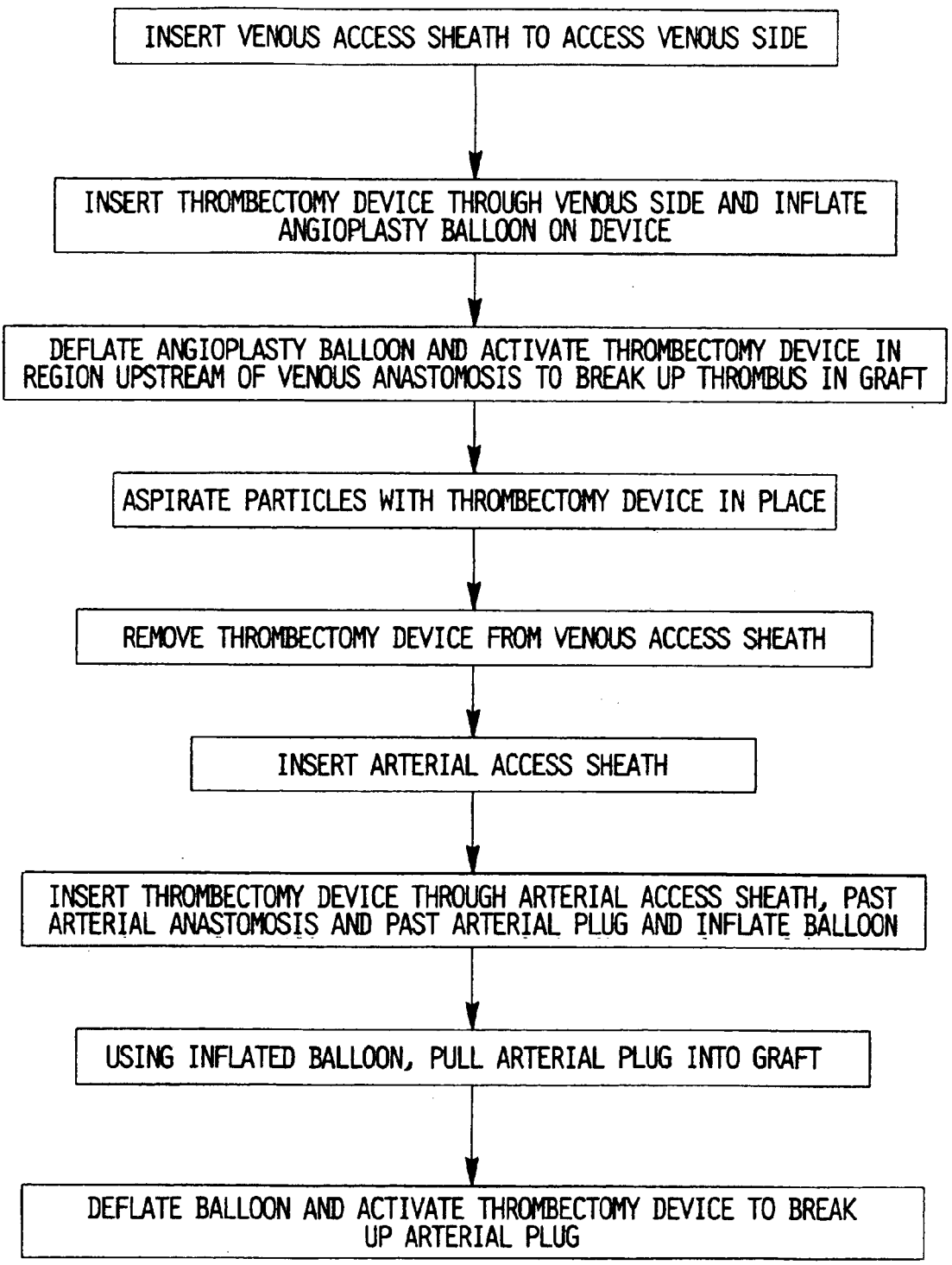

FIG_21
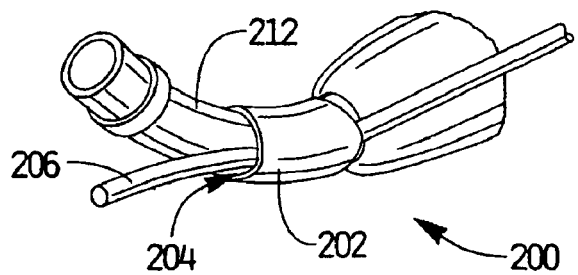
FIG_22
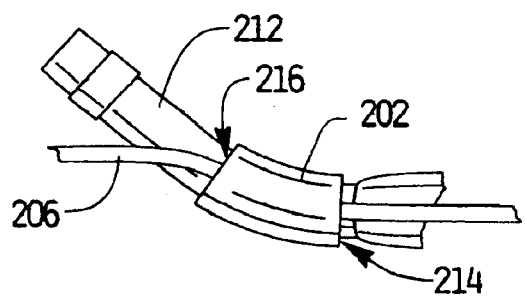
FIG_23
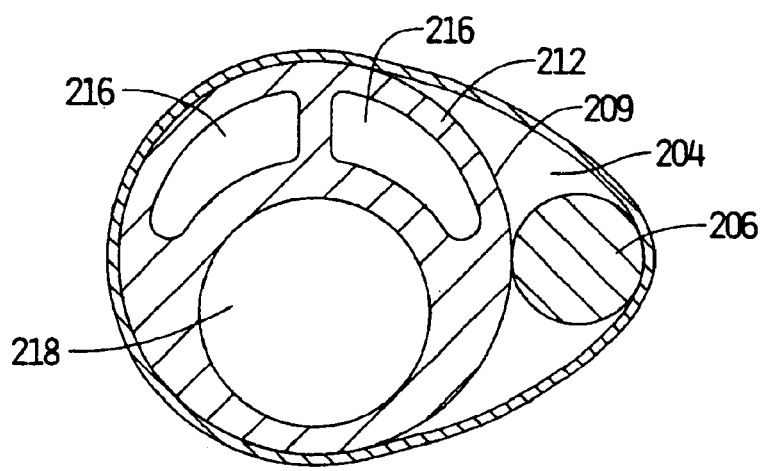

ROTATIONAL THROMBECTOMY DEVICE

This application is a continuation-in-part of application Ser. No. 09/502,261, filed Feb. 11, 2000, now U.S. Pat. No. 6,602,264, which is a continuation of application Ser. No. 09/122,483, filed Jul. 23, 1998, now U.S. Pat. No. 6,090,118, which claims priority from provisional application Ser. No. 60/053,475 filed Jul. 24, 1997, and is a continuation-in-part of application Ser. No. 09/888,149 filed Jun. 22, 2001, which is a continuation-in-part of International Application No. PCT/US00/41355, filed Oct. 20, 2000, which claims priority from provisional application Ser. Nos. 60/161,124, filed Oct. 22, 1999, and 60/214,331, filed Jun. 27, 2000. The entire contents of these applications are incorporated herein by reference.

BACKGROUND

1. Technical Field

This application relates to a vascular device and more particularly to a rotational thrombectomy device for clearing thrombus from dialysis grafts.

2. Background of Related Art

Hemodialysis is a well-known method of simulating renal (kidney) function by circulating blood. The kidneys are organs which function to extract water and urea, mineral salts, toxins, and other waste products from the blood with filtering units called nephrons. From the nephrons the collected waste is sent to the bladder for excretion. For patients suffering from chronic renal insufficiency, hemodialysis is life saving because it provides a machine to simulate the function of the kidneys, thereby enabling the patients to live independently between dialysis treatments.

In the hemodialysis procedure, blood is withdrawn from the patient's body and transported to a dialysis machine, also commonly referred to as a kidney machine. In the dialysis machine, toxins and other waste products diffuse through a semi-permeable membrane into a dialysis fluid closely matching the chemical composition of the blood. The filtered blood, i.e. with the waste products removed, is then returned to the patient's body.

In one approach, an arteriovenous fistula is created so a high rate of blood flows from the artery into the patient's vein. The blood is then withdrawn directly from the patient's vein (native vein fistula) providing high rates of blood flow. Since this approach requires multiple needle sticks in the vein to withdraw and return the blood, the vein can eventually be damaged beyond usability, blood clots can form and the vein can fail. Once the vein fails, it could no longer be used for access and an alternate site must be utilized.

To avoid the repetitive damage to the vein, dialysis grafts are used. These grafts, typically made of PTFE, are implanted under the patient's skin, typically in the patient's forearm, and the graft is sutured at one end to the vein (venous anastomosis) for outflow and at the other end to the artery (arterial anastomosis) for inflow. The graft is also typically a loop graft to provide greater access area. This graft, which functions as a shunt creating high blood flow from the artery to the vein, enables access to the patient's blood without having to directly puncture the vein. That is, the technician sticks the two needles into the graft to respectively withdraw and return blood to the patient, with the inlet on the arterial side for blood requiring filtration processing and the outlet on the vein side for return of processed blood from the dialysis machine.

The dialysis graft, while providing an advantageous arrangement for hemodialysis, may become inoperable after a period of time due to thrombus or clots formed as a result of the high rate of blood flow through the graft and repetitive injury at the venous anastomosis.

There have been various attempts to break up clots and other obstructing material in the graft. One approach is through injection of thrombolytic agents such as urokinase or streptokinase. These agents, however, are expensive, require lengthier hospital procedures and create risks of drug toxicity and bleeding complications as the clots are broken.

Other approaches to breaking up clots involve mechanical thrombectomy devices. For example, U.S. Pat. No. 5,766, 191 discloses a cage or basket composed of six memory wires that expand to press against the inner lumen to conform to the size and shape of the lumen. This multiple wire device is expensive and can be traumatic to the graft, possibly causing damage, since as the basket rotates, the graft is contacted multiple times by the spinning wires. Other risks associated with the basket include the possibility of catching onto the graft itself and tearing the graft as well as catching and tearing the suture at the anastomotic site. Additionally, the basket can become filled with a clot which would then require time consuming withdrawal of the basket, cleaning the basket and reinserting it into the lumen.

Commonly assigned U.S. Pat. No. 6,090,118, incorporated herein by reference, discloses a wire rotated to create a standing wave to break-up or macerate thrombus. The single wire is less traumatic than the aforedescribed basket device since it minimizes contact with the graft wall while still effectively mechanically removing thrombotic material.

This device of the '118 patent is effective in atraumatically and effectively breaking up blood clots. The present invention likewise provides a marked advance over the prior mechanical thrombectomy devices such as the baskets. The present invention achieves the same advantages as the device of the '118 patent, however, it utilizes a wire with a substantially sinuous configuration to create a wave-like rotational device. Thus, it provides the additional advantages of increased reliability and consistency in creating the wave pattern since the wave pattern created by the standing wave of the '118 patent will depend more on the rotational speed and the stiffness of the wire. Additionally, the sinuous configuration enables creation of a wave pattern at a lower rotational speed.

Co-pending commonly assigned U.S. patent application Ser. No. 09/888,149 incorporated herein by reference, discloses a thrombectomy device having a double balloon structure. This device advantageously reduces the number of individual catheters required to perform the thrombectomy procedure and reduces the number of surgical steps. The present invention therefore provides in one version a double balloon device with a sinuous wire configuration. The advantages of the double balloon thrombectomy device in simplifying the procedure and reducing operating costs is explained in more detail below in conjunction with the comparative flow charts of FIGS. 19–20.

SUMMARY

The present invention advantageously provides a thrombectomy apparatus for breaking up thrombus or other obstructive material in a lumen of a vascular graft or vessel comprising a flexible sheath and a wire of sinuous configuration positioned within the flexible sheath. The wire and flexible sheath are relatively movable so the wire assumes a sinuous configuration in a deployed configuration and assumes a straighter configuration in a non-deployed configuration. The wire is operatively connected to a motor for rotation of the wire to enable peaks of the sinuous wire to contact a wall of the lumen to break up the thrombus or other obstructive material.

Preferably, the wire is composed of an inner core and an outer layer. The inner core in one embodiment is formed by at least two wires twisted together. In a preferred embodiment, the distal portion of the flexible sheath is at an angle to a longitudinal axis of the sheath.

Preferably, the apparatus further includes a housing having a battery and a motor therein for causing rotation of the wire. In a preferred embodiment, a metal tube is operatively connected to the motor and the wire is connected to the metal tube such that rotation of the metal tube rotates the wire.

In one embodiment, the apparatus further includes first and second balloons and the flexible sheath has first and second lumens wherein the first lumen communicates with the first balloon and the second lumen communicates with the second balloon. In one of the double balloon embodiments, the first balloon is an angioplasty balloon and the second balloon is distal of the first balloon and configured for engaging and pulling an arterial plug into the graft.

The present invention also provides a thrombectomy apparatus comprising a flexible tube and a wire positioned within the flexible tube, wherein the wire and flexible tube are relatively slidable so the wire is movable between a substantially straightened position and a deployed position where it assumes a curved configuration. In the curved configuration the wire has a first arcuate region extending in a first direction and a second arcuate region spaced longitudinally from the first arcuate region extending in a second direction, wherein the first and second arcuate regions are configured to break up thrombotic material as the wire spins.

Preferably the wire is formed of an inner core of twisted wires and an outer layer.

In one embodiment, the apparatus includes an expandable balloon and the flexible tube contains a first lumen to receive the wire and a second lumen communicating with the balloon for injection of fluid to inflate the balloon.

The present invention also provides a thrombectomy apparatus comprising a flexible sheath and a wire rotatably positioned within the flexible sheath composed of at least one wire forming an inner core and at least one wire around the inner core to form an outer layer. The wire has a first arcuate region extending in a first direction, a second arcuate region extending in a second direction, and a substantially linear region, wherein the first and second arcuate regions break up thrombotic material in a vascular structure as the wire spins.

The present invention also provides a thrombectomy apparatus comprising a flexible tube, a wire of non-linear configuration positioned within the flexible tube and rotatable with respect to the flexible tube, first and second balloons inflatable to expand radially with respect to the flexible tube, and a motor for rotating the wire to break up the thrombotic material as the wire rotates (spins).

The present invention also provides a thrombectomy apparatus for performing a thrombectomy procedure to break up thrombus from a graft functioning as a shunt between an artery and a vein. The apparatus comprises a flexible catheter having a declotting mechanism to break up thrombotic or other obstructive material, a first angioplasty balloon inflatable to expand radially with respect to the flexible tube to perform angioplasty, and a second balloon inflatable to a configuration capable of pulling vascular material into the graft.

A method for breaking up thrombotic material from a lumen of a vascular graft or vessel is also provided. The method comprises:

inserting a sheath;

exposing a rotatable wire with respect to the sheath, the wire having a sinuous configuration; and rotating the wire so the peaks of the sinuous wire directly contact the graft wall as the wire spins.

A method for performing a thrombectomy procedure to break up thrombotic material in a vascular graft which forms a shunt between an artery and a vein is also provided. The method comprises:

inserting an introducer sheath;

providing a thrombectomy device having at least one inflatable balloon;

inserting the thrombectomy device through the introducer sheath and into a vascular graft;

inflating the at least one balloon to expand the balloon radially from the thrombectomy device;

deflating the balloon; and actuating the thrombectomy device to break up thrombotic material from the graft.

The method may further include the step of inflating a second balloon on the thrombectomy device.

BRIEF DESCRIPTION OF THE DRAWINGS

Preferred embodiment(s) of the present disclosure are described herein with reference to the drawings wherein:

FIG. 1 is an isometric view of the thrombectomy apparatus of the present invention showing the flexible sheath (tube) in the extended position to cover the rotational wire;

FIG. 2 is an isometric view similar to FIG. 1 except showing the flexible sheath retracted to expose the rotational wire to enable it to assume its sinuous configuration;

FIG. 4 is an enlarged side view of the distal region of the rotational wire of FIG. 2;

FIG. 5 is an enlarged side view of a portion of the wire of FIG. 4 showing the inner core and outer layer;

FIG. 6 is an enlarged side view of the distal tip of the wire of FIG. 4 showing an atraumatic tip attached to the wire;

FIG. 7 is side view showing the flexible sheath and knob for sliding the sheath with respect to the rotational wire;

FIG. 8 is an enlarged side view of the distal end of the flexible sheath of FIG. 7;

FIG. 9 is an isometric view of an alternate embodiment of the thrombectomy apparatus of the present invention having an angioplasty balloon and a distal balloon, showing the sheath in the advanced position to cover the rotational wire and further showing both balloons in the inflated condition for illustrative purposes;

FIG. 10 is a cross-sectional view taken along lines 10—10 of FIG. 9 showing the lumen configuration of the flexible sheath;

FIG. 11 is a side view of the flexible sheath and knob for sliding the sheath with respect to the rotational wire, and showing both balloons in the inflated condition for illustrative purposes;

FIG. 12 is an enlarged side view of a distal region of the apparatus of FIG. 9, showing both balloons inflated for illustrative purposes;

FIG. 13 is a perspective view showing a looped vascular graft connecting an artery and vein, a venous access sheath and an arterial access sheath extending into the graft, and the thrombectomy device of FIG. 9 inserted through the arterial sheath to access the venous side to perform an angioplasty procedure;

FIG. 14 illustrates the angioplasty balloon of the thrombectomy device of FIG. 9 inflated in the vascular graft to perform angioplasty;

FIG. 15 illustrates the thrombectomy device of FIG. 9 repositioned in the graft for operation of the wire to break up the blood clot;

FIG. 16 is a perspective view showing the thrombectomy device of FIG. 9 inserted through the venous access sheath to access the arterial side and the distal balloon inflated adjacent the arterial plug (clot);

FIG. 17 illustrates movement of the arterial plug into the vascular graft by the distal balloon;

FIG. 18 illustrates the rotational wire deployed to break up the arterial plug in the vascular graft;

FIG. 19 is a flow chart showing the steps of the prior art for removing thrombus from the vascular graft;

FIG. 20 is a flow chart showing the method steps of the present invention for removing thrombus utilizing the apparatus of FIG. 9;

FIGS. 21 and 22 are perspective and side views, respectively, of another alternate embodiment of the thrombectomy apparatus of the present invention showing the distal end portion containing shrink wrap tubing for receipt of a guidewire; and FIG. 23 is a cross-sectional view of the apparatus of FIG. 21 showing the guidewire alongside the apparatus.

DETAILED DESCRIPTION OF PREFERRED EMBODIMENTS

Figure 3:
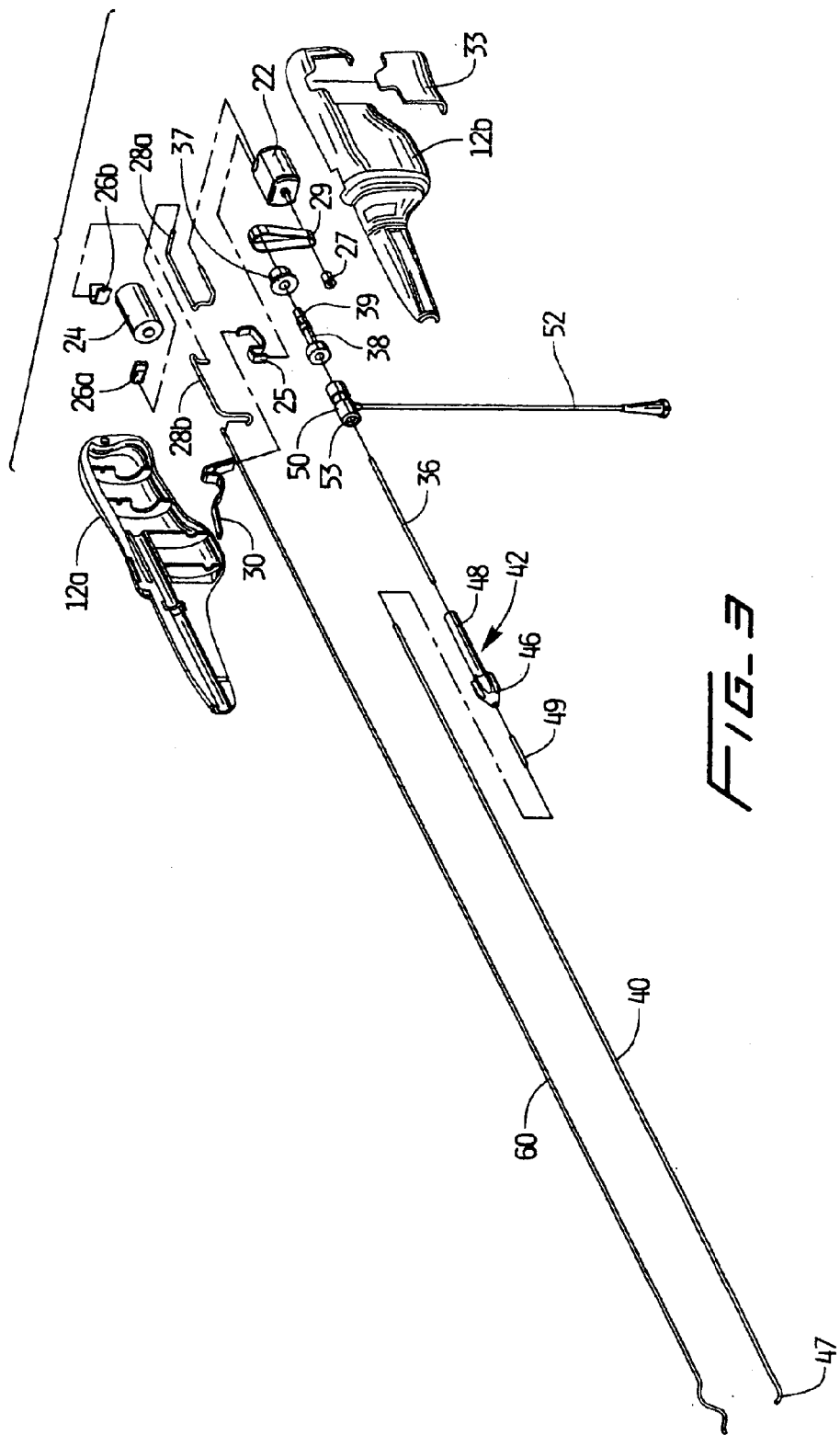
FIG. 3 is an exploded view of the thrombectomy apparatus of FIG. 1.

Referring now in detail to the drawings where like reference numerals identify similar or like components throughout the several views, FIGS. 1 and 2 illustrate a first embodiment of the thrombectomy apparatus of the present invention, designated generally by reference numeral 10.

Apparatus 10 has a housing 12 composed of housing halves 12a, 12b, a flexible tube or sheath 40 and a rotational thrombectomy wire 60 contained within the flexible sheath 40. A knob 42, extending from distal end 14 of housing 12, is attached to the flexible sheath 40 to enable both rotation and sliding movement of the flexible sheath (tube) 40 with respect to the wire which is fixed axially. Note that although the flexible sheath 40 is shown as slidable and the wire 60 is fixed axially, alternatively, the wire can be axially slidable with the sheath 40 stationary, or both the wire 60 and sheath 40 can be slidable. In any case, relative movement of the wire 60 and sheath 40 will enable the wire 60 to be exposed to assume the curved configuration described below to enable removal of obstructions, such as blood clots, from the lumen of the vascular structure, i.e. the vascular graft or the vessel wall.

With reference to FIG. 3, details of the internal structure of the apparatus 10 will be described. Contained within housing 12 is a motor 22 powered by a battery 24. Actuation button 30 is electrically connected to contact terminal 26b of battery 24 by button wire 28b; motor 22 is electrically connected to contact terminal 26a of battery 24 by battery wire 28a. Actuation button 30 is connected to motor 22 via wire strip 25 such that depression of button 30, which is accessible from the top portion of housing 12, turns on motor 22 to activate the apparatus. Battery door 33 can be provided to allow access to the battery 24.

Wire 60 is operatively connected to motor 22 via support tube 36 which is preferably composed of metal. Support tube 36 extends through opening 53 in Touhy borst 50 and into chuck 38, where a small set screw (not shown) extends through the outer wall of the chuck 38 to engage and compress the support tube 36 to maintain it in engagement with chuck 38. Belt 29 connects motor 22 to chuck pulley or speed reducing gear 37 to decrease the rotational speed, for example from 10,000 rpm to 3,000 rpm. Shaft 39 of chuck 38 extends through chuck pulley 37. Motor gear 27 engages chuck pulley or reducer gear 37. With this connection, when motor 22 is energized, the support tube 36 is rotated about its longitudinal axis, via rotation of chuck 38 driven by gears 27, 37, thereby rotating the wire 60 about its longitudinal axis. This rotation of wire 60 creates at least one vortex that macerates and liquefies the thrombus into small particles within the vascular lumen.

As noted above, flexible tube (sheath) 40 is slidable with respect to the housing 12 and wire 60. Flexible tube 40 is also rotatable. More specifically and with reference to FIGS. 3, 7 and 8, knob 42 has a gripping region 46 and a shaft 48, with a lumen extending therethrough. Strain relief 49 is frictionally fit, insert molded or attached by other suitable means to knob 42 and flexible tube 40 is connected to strain relief 49 (FIG. 3) by insert molding or other suitable means. With this attachment, sliding movement of knob 42 accordingly slides sheath 40 axially and rotation of knob 42 accordingly rotates sheath 40 about its longitudinal axis. Sliding movement of knob 42 exposes rotational wire 60, enabling it to assume its curved configuration; rotation of knob 42 orients the rotational wire 60 due to the J-shaped distal end of tube (sheath) 40, designated by reference numeral 47. The proximal end of gripping region 46 contains external threads (not shown) for threaded engagement with the distal end of housing 12 to lock the sheath 40 in the advanced position to maintain covering of the wire 60. Extension 48 of knob 42 has external threads (not shown) for threaded engagement within touhy 50 to lock the sheath 40 in the retracted position to maintain exposure of the wire.

The flexible sheath 40 can optionally contain one or more braided wires embedded in the wall to increase the stiffness. Such braided wires would preferably extend the length of the sheath 40, terminating proximal of the angled tip 47.

Touhy 50, having an extension arm 52, is positioned within housing 12 and has a lumen 53 communicating with the lumen of flexible sheath 40. Fluids, such as imaging dye can be injected through arm 52, flowing through sheath 40 in the space between wire 60 and the inner wall of the sheath 40, and exiting distal opening 41 to flow into the graft or vessel. This imaging dye provides an indication that fluid flow has resumed in the graft. Touhy 50 contains a conventional silicone gasket which is compressed when tightened to provide a seal to prevent back flow of fluid around the support tube 36. A radiopaque marker can be provided in the apparatus for imaging to visually locate the position of the apparatus.

Turning now to the rotational wire 60 and with particular reference to FIGS. 2 and 4–6, wire 60, in its expanded (deployed) configuration assumes a substantially sinuous configuration. This sinuous configuration resembles a sine curve.

As shown, wire 60 has a substantially linear portion extending through most of its length, from proximal region 62, through intermediate region 64 to distal region 66. At the distal region 66, wire 60 has a sinuous shape in that as shown it has a first arcuate region 63 facing a first direction (upwardly as viewed in the orientation of FIG. 3) and a second arcuate region 65, spaced longitudinally from the first arcuate region 63, facing a second opposite direction (downwardly as viewed in the orientation of FIG. 3). These arcuate regions 63, 65 form "peaks" to contact vascular structure as the wire 60 rotates. The distal tip 69 of wire 60 continues upwardly as a continuation of the "sine curve" configuration. An atraumatic tip 70, preferably composed of rubber, Pebax, or other elastomeric materials, although other materials are also contemplated, is insert molded or otherwise attached to the distalmost tip of the wire 60 to provide the apparatus 10 with an atraumatic distal tip to prevent damage to the graft or vessel wall during manipulation and rotation of the wire 60.

When the sheath 40 is in the advanced position, the curved regions of the wire 60 are compressed so the wire 60 (including the distal region 66) is contained in the tube 40 in a substantially straight or linear non-deployed configuration. This covering of the wire 60 by sheath 40 facilitates insertion through an introducer sheath and manipulation within the vascular structure. When the flexible sheath 40 is retracted by proximal axial movement of knob 42, the distal region 66 of the wire 60 is exposed to enable the wire 60 to return to its non-linear sinuous configuration shown in FIG. 2. The wire 60 is preferably composed of stainless steel which is pre-bent to the curved configuration of FIG. 4 and returns to this position when released from the flexible sheath 40.

In one embodiment, the wire 60 is composed of an inner core 61 and outer layer or coil 68. Inner core 61 can be formed by twisting three wires together in a tight configuration. Outer coil 68 is formed by winding a wire, preferably of larger diameter, to form an opening therethrough. Note the pitch of the outer coil 68 in region 67 increases as it is slightly stretched to facilitate attachment of the tip 70. In manufacture, the inner core 61 is slid within the opening of outer coil 68, and the core 61 and coil 68 are welded together at a proximal and distal end. This tightly wound outer/inner core structure enables rotation of the distal end of the wire 60 corresponding to rotation at its proximal end as torque is transmitted to the distal end. Rotation of the sinuous wire 60 results in a spiral path to simulate a multiple wire basket configuration, however with a reduced traumatic affect since contact with the vascular structure occurs a fraction of the time.

Various dimensions of the wire and flexible tube are contemplated. By way of example only, in one embodiment, where the flexible tube 40 has an outer diameter of about 0.062 inches, the curved regions of the wire 60 would extend from the longitudinal axis a distance of about 0.188 inches and the radius of curvature at region 65 would be about 0.376 inches in a wire having an overall diameter (combined outer coil and inner core) of about 0.035 inches. As can be appreciated, these dimensions are provided by way of example as other dimensions are also contemplated.

In use, the thrombectomy apparatus 10 is inserted into the graft (or vessel) through an access sheath and located via imaging. Once in the graft, the flexible sheath 40 of apparatus 100 can be rotated so the J-tip 47 is oriented to the desired position. Once in the desired position, the flexible sheath 40 is retracted, and button 30 is depressed to actuate motor 22, thereby causing support tube 36 and wire 60 to rotate about their longitudinal axis, causing the arcuate regions 63, 65 to directly contact and break up the thrombotic material inside the lumen of the graft (or vessel). Note that the location of the access sheaths for introducing the thrombectomy apparatus 10 can be appreciated by the illustration in FIG. 13 which shows use of apparatus 100 discussed below. Although the procedural steps differ between apparatus 10 and apparatus 100, the introducer sheath location could be the same. The introducer sheaths can optionally have side ports for aspirating the small macerated particles.

Alternate Embodiment—Thrombectomy Device with Balloon(s)

FIG. 9 illustrates an alternative embodiment of the thrombectomy apparatus of the present invention, designated generally by reference numeral 100. Thrombectomy apparatus 100 is similar to apparatus 10 of FIGS. 1–8, except for the provision of two inflatable balloons and two lumens in the catheter, each communicating with one of the balloons to allow passage of inflation fluid. Thus, the apparatus has a housing 112, a flexible sheath (tube) 140 and a rotational wire contained within sheath 140 identical in configuration and function to wire 60 of the FIG. 1. Knob 144 is rotatable to orient J-tip 146 and slides tube 140 to uncover the rotational wire in the same manner as knob 42 of FIG. 1. Note that FIGS. 9, 11 and 12 show both balloons inflated for illustrative purposes since in the preferred use of the apparatus as discussed in detail below, only one balloon would be inflated at a time.

The flexible sheath 140 of apparatus 100 has a lumen 110, illustratively circular in cross-section, for receiving the rotational wire 160, and first and second lumens 113, 114, each communicating with a balloon, for inflating the balloon. More specifically, first lumen 113 communicates with angioplasty balloon 120, which is preferably somewhat elliptical in shape, and second lumen 114 communicates with balloon 124, which is preferably substantially spherical in shape. Inlet ports 130, 132 communicate with lumens 113, 114, respectively, to inflate the respective balloons 120, 124.

The double balloon thrombectomy apparatus 100 reduces the procedural steps for thrombus removal and can be appreciated by comparison of the flow charts of FIGS. 19 and 20. In the prior art, two independent balloon catheters plus a mechanical thrombectomy device are required to perform a thrombectomy procedure; with the present invention, only one device, apparatus 100, is required.

More specifically and with reference first to the anatomical drawing of FIG. 13, a vascular graft G functions as a shunt between the artery A and vein V. Graft G is sutured to the artery at arterial anastomosis site 210 and is sutured to the vein at venous anastomosis site 212. A venous access sheath 218 is inserted on the arterial side and extends through the graft G to access the venous side; an arterial access sheath 214 is inserted in the venous side and extends through the graft G to access the arterial side.

Describing first the prior art method, which is not shown, and with reference to the flow chart of FIG. 19, an angioplasty balloon catheter is inserted through the venous access sheath and advanced to the venous anastomosis site, where the angioplasty balloon is inflated to treat the stenosis, i.e. expand the lumen by removing plaque. Then the angioplasty balloon is deflated and the balloon catheter is removed through the venous access sheath. Next a thrombectomy device is inserted through the venous access sheath into the graft. The thrombectomy device is then actuated to clear the thrombus and other obstructive material in the graft. The broken particles can then optionally be removed by suction with the thrombectomy device in place or after removal of the device from the graft.

Next, after removal of the thrombectomy device from the sheath, an arterial access sheath is inserted to access the arterial side. A balloon catheter, containing an expandable balloon such as a "Fogarty balloon", is inserted through the sheath and advanced past the arterial anastomosis so the tip is past the arterial plug (clot) adjacent the anastomosis site. The balloon, preferably composed of Latex, although other materials are contemplated, is inflated, and the balloon catheter is moved proximally to pull the arterial plug into the graft. The balloon is then deflated and the balloon catheter is removed through the arterial access sheath. The thrombectomy device is then inserted through the arterial access sheath into the graft, and actuated to break up the arterial plug. The particles can optionally be removed from the graft by suction with the thrombectomy device in place or removed from the sheath. The thrombectomy device is withdrawn from the arterial access sheath to complete the thrombectomy procedure.

As can be appreciated, this prior art method requires two balloon catheters in addition to the thrombectomy device. Further, this prior art method is time consuming since it requires four instrument insertions and removals: angioplasty balloon catheter, thrombectomy device, balloon catheter, and thrombectomy device.

With the thrombectomy device of FIG. 9 of the present invention, these numerous catheter insertions and removals are avoided. As depicted in the flow chart of FIG. 20, and as can be appreciated by the method drawings of FIGS. 13–18, fewer steps are required.

After the venous access sheath 218 is inserted, the thrombectomy device 100 which contains an angioplasty balloon 120 is inserted through the sheath (FIG. 13) so tip 146 extends past plaque P. Angioplasty balloon 120 is inflated via lumen 113 as shown in FIG. 14 to remove and compress the plaque P to open the lumen. The angioplasty balloon 120 is then deflated and the apparatus 100 is moved proximally so the rotational thrombectomy wire 160 is in the region of the graft G at the blood clot C as depicted in FIG. 15. The apparatus 100 is then activated to spin the sinuous wire 160 to break up the thrombus and other obstructive material. Suction can then optionally be applied either with the apparatus 100 in place, with the particles being removed through the gap between the flexible sheath 140 and the introducer sheath 218, or the apparatus 100 can be removed and suction applied through the sheath 218.

After breaking up the blood clot, apparatus 100 is removed from venous access sheath 218 and inserted through arterial access sheath 214. The apparatus 100 is inserted so the tip extends slightly beyond the arterial anastomotic site 210, past the arterial plug (clot) D, and the spherical distal balloon 124 on apparatus 100 is inflated (FIG. 16). The apparatus 100 is then pulled proximally so that balloon 124 pulls the arterial plug D into the graft G (FIG. 17). The thrombectomy apparatus 100 can then be actuated to rotate wire 160 to break up the clot D (FIG. 18) and other obstructive material, and optionally the broken particles can be removed by suction as described above. The thrombectomy apparatus 100 is then removed through arterial access sheath 214, completing the thrombectomy procedure.

It is also contemplated that as an alternative to the double balloon thrombectomy device, a single balloon device can be provided. This device could contain either angioplasty balloon 120 or balloon 124. If only balloon 120 is provided, although the procedure would still require a separate balloon catheter to remove the arterial plug, it would still advantageously eliminate the step and expense of a separate angioplasty catheter. Alternatively, if the single balloon device contained only balloon 124, although the procedure would require a separate angioplasty balloon catheter, it would still advantageously eliminate the step and expense of a separate balloon catheter for pulling the arterial plug into the graft.

It should also be appreciated that the double balloon concept to facilitate and expedite the surgical thrombectomy procedure can be utilized with other thrombectomy devices. For example, mechanical thrombectomy devices utilizing rotating wire baskets, fluid jet (hydrodynamic) devices applying high pressure fluid, devices utilizing brushes having bristles to scrape the clot and devices with rotating impellers can be modified to incorporate one or more balloons, i.e. an angioplasty and/or distal balloon to perform an angioplasty procedure and/or pull an arterial plug into the graft.

In the alternate embodiment of the thrombectomy apparatus in FIGS. 21–23, apparatus 200 (only the distal portion is shown) is identical to apparatus 100 except for shrink-wrap tubing 202 around a distal portion of the apparatus 100 to form an opening or lumen 204 for a guidewire. A guidewire 206 would be inserted through the arterial access sheath and past the stenosis (arterial clot). The guidewire 206 would then be threaded through the lumen 204 formed between tubing 202 and the outer surface 209 of flexible sheath 212 (which contains inflation lumens 216 and lumen 218 for the rotational wire). Guidewire 206 enters at entrance port 216 and exits through exit port 214, to extend along the length of flexible sheath 212. In this manner, this rapid exchange feature would allow the apparatus 200 to be more easily advanced past the arterial plug or stenosis as it is threaded over the guidewire.

As an alternative to the shrink wrap tubing forming the guidewire lumen, the catheter could be provided with an additional lumen formed therein, extending a short distance at the distal end portion, to accommodate the guidewire.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A thrombectomy apparatus for breaking up thrombus or other obstructive material in a lumen of a vascular graft or vessel, the apparatus comprising:

a flexible sheath extending in an axial direction;

a wire positioned within the flexible sheath; and a motor operatively connected to the wire;

the wire and the flexible sheath being relatively movable in the axial direction so that the wire has a first configuration when positioned within the flexible sheath and a second configuration when deployed from the flexible sheath, the wire having a sinuous shape in the second configuration and a straighter shape in the first configuration, the wire being rotatable by the motor to enable peaks of the wire in the sinuous shape to contact a wall of the lumen to break up the thrombus or other obstructive material.

2. The thrombectomy apparatus of claim 1, wherein the wire includes an inner core and an outer coil.

3. The thrombectomy apparatus of claim 2, wherein the inner core is formed by at least two wires twisted together.

4. The thrombectomy apparatus of claim 2, wherein the inner core is welded within the outer coil at proximal and distal ends.

5. The thrombectomy apparatus of claim 1, wherein the wire includes a plurality of wires twisted together.

6. The thrombectomy apparatus of claim 1, further comprising a soft blunt tip affixed to a distal end of the wire.

7. The thrombectomy apparatus of claim 6, wherein a distal portion of the flexible sheath is at transverse angle to the axial direction of the sheath.

8. The thrombectomy apparatus of claim 1, further comprising a housing, the housing including the motor and a battery for supplying power to the motor, the wire extending from the housing.

9. The thrombectomy apparatus of claim 8, further comprising a metal tube operatively connected to the motor, the wire being connected to the metal tube such that rotation of the metal tube rotates the wire.

10. The thrombectomy apparatus of claim 1, further comprising first and second balloons, wherein the flexible sheath has first and second lumens, the first lumen communicating with the first balloon and the second lumen communicating with the second balloon.

11. The thrombectomy apparatus of claim 10, wherein the first balloon is an angioplasty balloon and the second balloon is configured for engaging and pulling an arterial plug, the first balloon being proximal of the second balloon.

12. The thrombectomy apparatus of claim 1, further comprising an angioplasty balloon expandable radially with respect to the flexible sheath.

13. The thrombectomy apparatus of claim 1, further comprising an inflatable balloon for engaging and pulling an arterial plug into the lumen of the graft, the balloon being expandable radially with respect to the flexible sheath.

14. A thrombectomy apparatus for breaking up thrombotic material in a vascular structure, the apparatus comprising:
   a flexible sheath extending in an axial direction;
   a rotatable wire positioned within the flexible sheath; and
   a motor operatively connected to the wire;
   the wire and the flexible sheath being relatively slidable in the axial direction so that the wire is movable between a substantially straightened configuration when positioned within the flexible sheath and a curved configuration when deployed from the flexible sheath, in the curved configuration the wire having a first arcuate region extending in a first direction and a second arcuate region spaced in the axial direction from the first arcuate region and extending in a second direction, the wire being rotatable by the motor to enable the first and second arcuate regions to break up the thrombotic material in the vascular structure.

15. The thrombectomy apparatus of claim 14, wherein the wire is formed of an inner core of twisted wires and an outer coil.

16. The thrombectomy apparatus of claim 15, further comprising an expandable balloon, wherein the flexible sheath contains a first lumen to receive the wire and a second lumen communicating with the balloon for injection of fluid to inflate the balloon.

17. A thrombectomy apparatus for breaking up thrombotic material in a vascular structure, the apparatus comprising:
   a flexible sheath extending in an axial direction;
   a thrombectomy wire rotatably positioned within the flexible sheath, the thrombectomy wire including at least one wire forming an inner core and at least one wire wound around the inner core to form an outer layer, the thrombectomy wire having a first arcuate region extending in a first direction, a second arcuate region extending in a second direction, and a substantially linear region; and
   a motor operatively connected to the thrombectomy wire, the thrombectomy wire being rotatable by the motor to enable the first and second arcuate regions to break up the thrombotic material in the vascular structure.

18. A thrombectomy apparatus for breaking up thrombotic material in a vascular structure, the apparatus comprising:
   a flexible tube;
   a wire having a non-linear configuration positioned within the flexible tube and being rotatable with respect to the flexible tube;
   first and second balloons connected to the flexible tube and being inflatable to expand radially with respect to the flexible tube; and
   a motor operatively connected to the wire for rotating the wire to break up the thrombotic material in the vascular structure.

19. A thrombectomy apparatus for performing a thrombectomy procedure to break up thrombus from a graft functioning as a shunt between an artery and a vein, the apparatus comprising:
   a flexible catheter having a declotting mechanism to break up thrombotic material or other obstructive material;
   a first angioplasty balloon connected to the flexible catheter and being inflatable to expand radially with respect to the flexible catheter into a first configuration to perform an angioplasty procedure; and
   a second balloon connected to the flexible catheter and being inflatable to a second configuration capable of pulling vascular material into the graft, the second configuration being different from the first configuration.

20. A method for breaking up thrombotic material from a lumen of a vascular graft or vessel, the method comprising:
   inserting a sheath into the lumen;
   deploying a wire with from the sheath, the wire having a first configuration when positioned within the sheath and a second configuration when deployed from the sheath, the wire having a sinuous shape in the second configuration and a straighter shape in the first configuration; and
   rotating the wire so that peaks of the wire in the sinuous shape directly contact a wall of the lumen to break up the thrombotic material.

21. A method for performing a thrombectomy procedure to break up thrombotic material in a vascular graft which forms a shunt between an artery and a vein, the method comprising:
   inserting an introducer sheath into the vascular graft;
   providing a thrombectomy device having a flexible sheath extending in an axial direction, a wire positioned within the flexible sheath, a motor operatively connected to the wire, and at least one inflatable balloon connected to the flexible sheath, the wire and the flexible sheath being relatively movable in the axial direction so that the wire has a first configuration when positioned within the flexible sheath and a second configuration when deployed from the flexible sheath, the wire having a sinuous shape in the second configuration and a straighter shape in the first configuration;
   inserting the thrombectomy device through the introducer sheath and into a vascular lumen;

inflating the at least one balloon to expand the balloon radially from the thrombectomy device;

deflating the balloon; and actuating the motor to rotate the wire to enable peaks of the wire in the sinuous shape to contact a wall of the vascular graft to break up thrombotic material in the vascular graft.

22. The method of claim 21, wherein the step of actuating the thrombectomy device comprises exposing a rotatable wire and rotating the wire.

23. The method of claim 22, wherein the thrombectomy device includes a second balloon, and the method includes inflating the second balloon.

* * * * *